(12) United States Patent
Linardos et al.

(10) Patent No.: US 7,890,887 B1
(45) Date of Patent: Feb. 15, 2011

(54) SYSTEM AND METHOD FOR THE OPERATION OF DIAGNOSTIC MEDICAL EQUIPMENT

(75) Inventors: John Linardos, Smithtown, NY (US); Godfrey Vassallo, Northport, NY (US); Jevan Damadian, East Northport, NY (US); Jayne J Cohen, New Hyde Park, NY (US)

(73) Assignee: Fonar Corporation, Melville, NY (US)

( * ) Notice: Subject to any disclaimer, the term of this patent is extended or adjusted under 35 U.S.C. 154(b) by 2581 days.

(21) Appl. No.: 10/094,589

(22) Filed: Mar. 7, 2002

Related U.S. Application Data

(60) Provisional application No. 60/273,636, filed on Mar. 7, 2001.

(51) Int. Cl.
 *G06F 3/00* (2006.01)
(52) U.S. Cl. .................. 715/810; 715/864; 715/760; 715/763; 709/236; 709/245
(58) Field of Classification Search .......... 715/810, 715/764, 700, 763, 864, 760; 709/231, 242, 709/236, 245; 324/320, 324
See application file for complete search history.

(56) References Cited

U.S. PATENT DOCUMENTS 6,157,194 A 12/2000 Vassallo et al.

| | | | |
|---|---|---|---|
| 6,283,761 B1 * | 9/2001 | Joao | 434/236 |
| 6,366,094 B1 | 4/2002 | Vassallo et al. | |
| 6,496,477 B1 * | 12/2002 | Perkins et al. | 370/228 |
| 6,598,011 B1 * | 7/2003 | Howards Koritzinsky et al. | 702/185 |
| 6,928,490 B1 * | 8/2005 | Bucholz et al. | 709/249 |

* cited by examiner

*Primary Examiner*—Kieu Vu
*Assistant Examiner*—Michael Roswell
(74) *Attorney, Agent, or Firm*—IP Strategies

(57) ABSTRACT

A system that allows a technician to remotely control interactive equipment, such as medical diagnostic and screening equipment, by executing, through a proxy program, those portions of the software that directly interact with the equipment at the local computer for the equipment. The software components that do not interact with the equipment are run on the local computer. This communication linkage is established through a library module, which can detect when a program must communicate through the proxy. Thus, the same software modules can operate locally as well as remotely. This design distributes the processing so that a user interface is provided to the remote operator that is the same as the user interface that would be provided to the local operator. In addition to the user interface, the functionality of the equipment enabled at the remote space is the same as that available locally at the equipment.

34 Claims, 7 Drawing Sheets

SYSTEM AND METHOD FOR THE OPERATION OF DIAGNOSTIC MEDICAL EQUIPMENT

CROSS-REFERENCE TO RELATED APPLICATIONS

This is related to U.S. Provisional Patent Application Ser. No. 60/273,636, which was filed on Mar. 7, 2001, the entire disclosure of which is incorporated herein.

FIELD OF THE INVENTION

The present invention relates in general to remotely controlling equipment that requires interaction with a skilled operator to perform its function. As a particular example, the present invention relates to such equipment in the medical field, such as scanning and imaging systems for performing medical diagnoses using nuclear magnetic resonance imaging ("MRI"), which conventionally require technicians at the scanning location to perform the scanning function. According to the present invention, scanning technicians can control at least some aspects of the scanning procedure remotely over a communications channel.

BACKGROUND OF THE INVENTION

Many types of equipment require interaction with a skilled operator to perform the function of the equipment. For example, the medical field uses various types of equipment to screen and diagnose illness in patients, who may be humans or animals. Interaction is necessary, because parameters and settings particular to the patient must be entered before the procedure can begin. Then, after a phase of the procedure has finished, results must be examined, and possibly parameters changed, to determine if the phase must be repeated before moving on to the next phase. The next phase itself might require parameter changes or action by the patient before proceeding.

One type of such equipment is an MRI scanner. MRI systems conventionally require an on-site technician to run the equipment and interact with the patient. Scanning parameters that typically must be controlled include scan sequence selection, field of view, slice thickness, number of slices, and number of excitations. Further, the technician typically positions the patient in the scanner, places an imaging coil on the patient, and interacts with the patient in order to determine his/her comfort level. Conventionally, the technician views the scan to determine its quality and, if necessary, adjusts one or more parameters and re-runs the scan. When the scan is completed to the technician's satisfaction, the technician will prepare the images for filming by, for example, adjusting brightness and contrast, and panning and zooming selected images. The technician might run several scans, each targeting a different view of the patient, and can prepare the images after scanning each view, or in a batch after all views have been scanned.

This is a labor-intensive procedure, and contributes to the high cost of MRI scanning and diagnosis. Some hospitals are large and require more than one machine; conventionally, these hospitals must have a technician present at each machine. Other hospitals are small, and have a single machine, but don't use it enough for it to be cost-effective to have a full-time technician present at the machine.

Conventional techniques for MRI scanner operation are performed locally. The ability exists to send images over the Internet and other networks, but no capability to actually operate the scanner remotely. Using present systems, a local technician operates the scanner and the images are displayed locally. Additionally, the images can be sent via the Internet or local area network to a remote display system. The remote display system is used only for displaying, windowing, and archiving images and data, but doesn't have the ability to manipulate or operate the scanner, and does not monitor the local scanning area.

It would be advantageous for a large hospital to have centralized control for all the MRI scanners. It would also be advantageous for a single technician to have the ability to control a number of MRI scanners at a respective number of small hospitals. Alternatively, it would be advantageous for a single, or a few, MRI scanners to be located at a central location and shared by a number of small hospitals, so that each hospital can have a local technician to control scanning and imaging from the hospital.

However, due to difficulties in controlling medical diagnostic equipment, the number of parameters that must be set, the need for interaction with patients, the complicated nature of the process, and the lengthy set-up required for a scan process, remote scanner control has not been realized.

BRIEF SUMMARY OF THE INVENTION

The invention is a system that allows a technician to remotely control an MM scanner. The system of the present invention achieves this remote control capability by executing, through a proxy program, those portions of the software that directly interact with the MRI hardware at the MRI scanner computer. The software components that do not interact with the scanner are run on the local computer. Programs that must interact with peripheral components of the scanner also use the proxy program. This communication linkage is established through a library module, which can detect when a program must communicate through the proxy. Thus, the same software modules can operate locally as well as remotely. This design distributes the processing so that a user interface is provided to the remote operator that is the same as the user interface that would be provided to the local operator. In addition to the user interface, the functionality of the MRI scanner related to scanning and image process enabled at the remote space is the same as that available locally at the scanner. Distributing the processing in this manner also minimizes utilization of bandwidth on the communications channel used.

The invention is also a method of controlling an MRI scanner and remotely viewing MRI image. According to the process of the invention, a technician at a location that is remote from the scanner location supervises preparation of the patient by a local assistant, initializes the scanner, runs the scan procedure, reviews images, and saves image data, much as a technician at the scanner would perform the process. The flexibility provided by the present invention allows the remote technician, the scanner, and the image storage space to be located anywhere with respect to each other. The different spaces can be separated by floors within the same building, or can be located in different buildings in completely different geographical areas.

The invention is also a communications protocol (data structure) by which the processor at the control location and the processor at the scan location communicate to allow control of the scan procedure to be assumed by the remote technician. The protocol allows the control processor to provide commands to the scan processor to initialize the scanner, run a scanning procedure, and terminate a scanning session.

The invention is also a cooperative business method of pooling personnel and equipment resources for performing MRI diagnostic scanning and imaging, to provide a shared capability that does not exist with conventional scanning systems. This capability provides advantages, for example, in rural areas where scanners and scanning technicians are in short supply. According to the business method of the present invention, a technician's skills can be shared by widely dispersed communities. Likewise, scanner resources can be shared within communities, by allowing a technician to control several scanners within, for example, a metropolitan region.

The invention is also a storage medium including instructions for causing a data processor to control a MRI system remotely via a network or other communications channel. This storage medium can include instructions for the remote scan controller, the scanner processor, or both, and can be, for example, a magnetic medium or an optical medium.

According to the various aspects of the present invention, an MRI operator or other technician has the ability to operate an MRI scanner, and view resulting images, from a remote location. The system of the invention allows control of an MRI scanner via a network, which can be a LAN, WAN, MAN, satellite network, an intranet, the Internet, or any other data network, or by way of a dedicated connection, such as a wired link or by dedicated satellite communication. Images resulting from the scan, or from a scan that is locally controlled, can be remotely viewed via the network as well. Thus, an operator can remotely perform tasks that he or she would otherwise perform locally, that is, while physically present at the scanning center. The remote operator can monitor activity at the scanning center through the use of video signals sent over the network and prepare patients for scanning with the help of an assistant stationed at the scanner. It is not required for the assistant to have the same level of training as the technician, because his/her actions will be directed and monitored by the technician. The present invention can be used by other medical personnel, such as radiologists to perform remote scans, physicians and surgeons to direct the scan procedure and make diagnoses, a scanning technician to operate more than one scanner, and research scientists to use remote scanners for research purposes. The present invention can also be used by service personnel to perform maintenance operations on the equipment, or to diagnose errors or even fix the equipment when it is malfunctioning.

A highly skilled radiologist or scanning technician in one location can control and supervise the operation of a scanner in another location, regardless of the distance. In addition, a highly skilled scanning technician can operate many scanning centers from a central location, thereby reducing the overall operating expenses of the scanning centers.

Exemplary embodiments of the invention include a local MRI scanner, a network connection (for example, a local area network, wide area network, metropolitan area network, satellite network, intranet, Internet) and a remote scan control console to enable a remote operator to have control of at least some aspects of an MRI scanner. For example, by using the Internet through a broadband connection, a remote, high-speed link between the remote control subsystem and the MRI scanner subsystem is achieved. Utilizing a LAN would be practical for controlling several MM scanners within a single hospital, whereas connection via the Internet or a satellite network might be necessary over greater distances. Use of the Internet is advantageous in that a standard protocol is used, so that control subsystems and scanner subsystems can be connected to an existing cooperative system quickly and easily, and new systems can be initiated by providing an Internet connection at a controller computer and at a scanner computer, and by installing the appropriate control software at each location.

According to a particular aspect of the present invention, a system for controlling interactive equipment from a location that is remote from the equipment includes a user interface that accepts inputs from a user and provides corresponding user input signals, a control processor, in communication with the user interface, that receives the user input signals and formats the user input signals for transmission, an equipment processor, in communication with the interactive equipment, that receives the formatted user input signals and controls the interactive equipment based on at least some of the formatted user input signals, and a communications channel that provides a communications capability between the control processor and the equipment processor, such that the formatted user input signals can be transmitted from the control processor to the equipment processor. The interactive equipment can be medical diagnostic equipment or medical screening equipment, which in turn can be an MRI scanner. The communications channel can be a network, which in turn can be a local area network, a wide area network, a metropolitan area network, a satellite network, an intranet, or the Internet. Alternatively, the communications channel can be a dedicated channel, such as a wired link, an infrared link, a radio frequency link, and a satellite link. The user interface can include at least one of an input device and an output device. The input device can be any combination of, for example, keyboards, cursor pointers, microphones, video cameras, and touch screen devices. The output device can be any combination of, for example, video monitors and audio speakers. The equipment processor can include a proxy server that receives the formatted user input signals and controls the interactive equipment based on at least some of the formatted user input signals. The proxy server translates the formatted user input signals to provide control inputs for the interactive equipment. The equipment processor can include at least one peripheral module. The at least one peripheral module can include at least one of a validation pulse sequence module, a scanning pulse sequence module, and a tuning sequence module. The user interface can communicate with the at least one peripheral module via the proxy server. The proxy server conducts serial communication with said at least one peripheral module for the user interface. The user interface can include an equipment user interface that provides formatted operational user input signals to the proxy server, wherein at least some of the formatted user input signals include the formatted operational user input signals. The formatted operational user input signals can control at least initiation and termination of procedures performed by the interactive equipment. The formatted operational user input signals can include operational parameters used by the interactive equipment. The user interface can include a control module that provides formatted adjustment user input signals to the proxy server, wherein at least some of the formatted user input signals include the formatted adjustment user input signals. The formatted adjustment user input signals can include at least one of a power amplifier adjustment, a receiver gain, and a central frequency. The equipment processor can include at least one peripheral module. The at least one peripheral module can include at least one of a validation pulse sequence module, a scanning pulse sequence module, and a tuning sequence module. The control module can communicate with the at least one peripheral module via the proxy server. The proxy server can conduct serial communication with said at least one peripheral module for the control module. The equipment processor can include a database server that communicates with at least one database for the diagnostic medical equipment, and the user interface can include an equipment user interface that enters data into at least one of said at least one database through the database server. The equipment processor can include a database server that communicates with at least one database for the diagnostic medical equipment, and the user interface can include an equipment user interface that receives data from at least one of said at least one database through the database server. The received data can be status information, and the user interface can include a monitor that displays the status information. The equipment processor can include a database server that communicates with at least one database for the diagnostic medical equipment, and the user interface can include a display system that receives data from at least one of said at least one database through the database server. The received data can be image data, and the user interface can include a monitor that displays images corresponding to the received image data. The user interface can be coupled for communication with a storage medium and can provide the received image data to the storage medium. The display system can include a modification module for performing enhancing, zooming, windowing, or filming the displayed images in accordance with inputs provided by the user. The system can also include a library module that detects the formatted user input signals and enables the interactive equipment to be controlled based on at least some of the formatted user input signals.

According to another aspect of the present invention, a method of controlling interactive equipment includes establishing a communications channel between the interactive equipment and a remote controller space, sending a formatted initiation command to the interactive equipment from the remote controller space to initiate a diagnostic procedure at the interactive equipment, allowing the diagnostic procedure to terminate, storing result data generated by the diagnostic procedure, and breaking the communications channel. The method can further include sending formatted initialization data to the interactive equipment from the remote controller space, prior to sending the formatted initiation command. The initialization data can include set-up parameters. The initialization data can include parameter settings and parameter adjustment values. The method can further include reviewing the result data at the remote controller space, prior to storing the result data. Reviewing the result data can include determining if the result data meets diagnostic acceptance criteria. The method can further include resending the formatted initiation command, if it is determined that the result data does not meet the diagnostic acceptance criteria. The result data can be image data. The can further include preparing a subject patient for the diagnostic procedure, prior to sending the formatted initiation command. Preparing the subject patient for the diagnostic procedure can include speaking to the patient via the communications channel, or positioning the patient with respect to the interactive equipment. The method can further include repositioning the subject patient, after allowing the diagnostic procedure to terminate, and sending a second formatted initiation command to the interactive equipment from the remote controller space to initiate a second diagnostic procedure at the interactive equipment. Allowing the diagnostic procedure to terminate can include sending a formatted termination command to the interactive equipment from the remote controller space. Establishing a communications channel between the interactive equipment and a remote controller space can include relinquishing local control of the diagnostic procedure by the interactive equipment and allowing the remote controller space to take control of the diagnostic procedure. Establishing a communications channel between the interactive equipment and a remote controller space can include connecting the interactive equipment and the remote controller space on a data network. Establishing a communications channel between the interactive equipment and a remote controller space can include connecting the interactive equipment and the remote controller space via the Internet. The interactive equipment can be medical diagnostic equipment or medical screening equipment, which in turn can be an MRI scanner. The method can further include monitoring video images of the interactive equipment, while the communications channel is established. Storing the result data can include formatting the result data for transmission, and transmitting the formatted result data to a remote storage medium. The method can further include communicating with at least one peripheral of the interactive equipment during the diagnostic procedure.

According to another aspect of the present invention, in a system for controlling interactive equipment according to a control signal from a location that is remote from the equipment, a data structure for the control signal includes a communications protocol for transmitting and receiving the control signal from the remote location to the interactive equipment over a communications channel, and operational information used by the interactive equipment for controlling the interactive equipment. The operational information can be grouped in packets that are wrapped in the communications protocol. The communications channel can be a data network, and the communications protocol can include information necessary for data transmission over the data network. The data network can be the Internet, in which case the communications protocol is TCP/IP. The communications channel can be a satellite link, in which case the communications protocol includes information necessary for data transmission over the satellite link. The operational information can include at least one of command information and parameter data. The command information can include a run command, to initiate a diagnostic procedure at the interactive equipment, and a terminate command, to terminate a diagnostic procedure at the interactive equipment. The interactive equipment can be medical diagnostic equipment or medical screening equipment, which in turn can be an MRI scanner. The parameter data can include scan sequence selection, field of view, slice thickness, number of slices, and number of excitations. The operational information can be specific to a manufacturer of the interactive equipment. The interactive equipment can be medical diagnostic equipment or medical screening equipment, which in turn can be an MRI scanner.

According to another aspect of the present invention, a cooperative business method of pooling personnel and equipment resources for performing interactive medical procedures includes establishing a network of interactive medical equipment and control space by creating a communications channel between at least one of interactive medical equipment and control space and another of interactive medical equipment and control space, enabling control of a diagnostic procedure at the interactive medical equipment by a user at the control space over the communications channel, and performing an interactive medical procedure at the interactive medical equipment, under the control of the user at the control space, by way of formatted control signals transmitted over the communications channel. At least one of interactive medical equipment and control space includes a plurality of interactive medical equipment. The business method can further include sending, by the user at the control space, the formatted control signals to any of the plurality of interactive medical equipment over the communications channel, to perform the interactive medical procedure at the respective interactive medical equipment under the control of the user. The business method can further include generating output data as a result of the interactive medical procedure. The business method can further include storing the output data in a storage medium. The storage medium can be connected to the communications channel between at least one of the interactive medical equipment and the control space, and storing the output data can include formatting the output data for transmission to the storage medium over the communications channel. The storage medium can be a selected one of a plurality of storage media connected to the communications channel. The output data can be video data. The at least one of interactive medical equipment and control space can include a plurality of control spaces. The business method can further include sending, by the user located at any of the plurality of control spaces, the formatted control signals to the interactive medical equipment over the communications channel, to perform the interactive medical procedure at the interactive medical equipment under the control of the user. The business method can further include generating output data as a result of the interactive medical procedure. The business method can further include storing the output data in a storage medium. The storage medium can be connected to the communications channel between said at least one of interactive medical equipment and control space, and storing the output data can include formatting the output data for transmission to the storage medium over the communications channel. The storage medium can be a selected one of a plurality of storage media connected to the communications channel. The output data can be video data. The at least one of interactive medical equipment and control space can include a plurality of interactive medical equipment and a plurality of control spaces. The business method can further include sending, by the user located at any of the plurality of control spaces, the formatted control signals to a selected one of the plurality of interactive medical equipment over the communications channel, to perform the interactive medical procedure at the selected one of the plurality of the respective interactive medical equipment under the control of the user. The business method can further include generating output data as a result of the interactive medical procedure. The business method can further include storing the output data in a storage medium. The storage medium can be connected to the communications channel between said at least one of interactive medical equipment and control space, and storing the output data can include formatting the output data for transmission to the storage medium over the communications channel. The storage medium can be a selected one of a plurality of storage media connected to the communications channel. The output data can be video data. Creating a communications channel can include connecting for communication via the Internet. The interactive medical equipment can be an MRI scanner.

According to another aspect of the present invention, a storage medium includes instructions for causing a data processor to control interactive equipment remotely via a network. The instructions include sending a formatted initiation command to the interactive equipment from a remote controller space to initiate a diagnostic procedure at the interactive equipment, allowing the diagnostic procedure to terminate, and storing result data generated by the diagnostic procedure. The instructions can further include sending formatted initialization data to the interactive equipment from the remote controller space, prior to sending the formatted initiation command. The initialization data can include set-up parameters. The initialization data can include at least one of parameter settings and parameter adjustment values. The instruction of allowing the diagnostic procedure to terminate can include sending a formatted termination command to the interactive equipment from the remote controller space. The instructions can further include relinquishing local control of the diagnostic procedure by the interactive equipment and allowing the remote controller space to take control of the diagnostic procedure. The interactive equipment can be one of medical diagnostic equipment and medical screening equipment, which in turn can be an MRI scanner. The instruction of storing the result data can include formatting the result data for transmission and transmitting the formatted result data to a remote storage medium. The storage medium can further include communicating with at least one peripheral of the interactive equipment during the diagnostic procedure. The storage medium can include several instances of storage media. The storage medium can be one of a magnetic medium and an optical medium.

DETAILED DESCRIPTION OF THE INVENTION

According to the various aspects of the present invention, an MRI operator or other technician has the ability to operate an MRI scanner, and view resulting images, from a remote location. The operator can also direct the storage of the scanned image data, at any combination of locations, such as at the local scanning space, at the remote control space, and at a different remote location.

Figure 1:
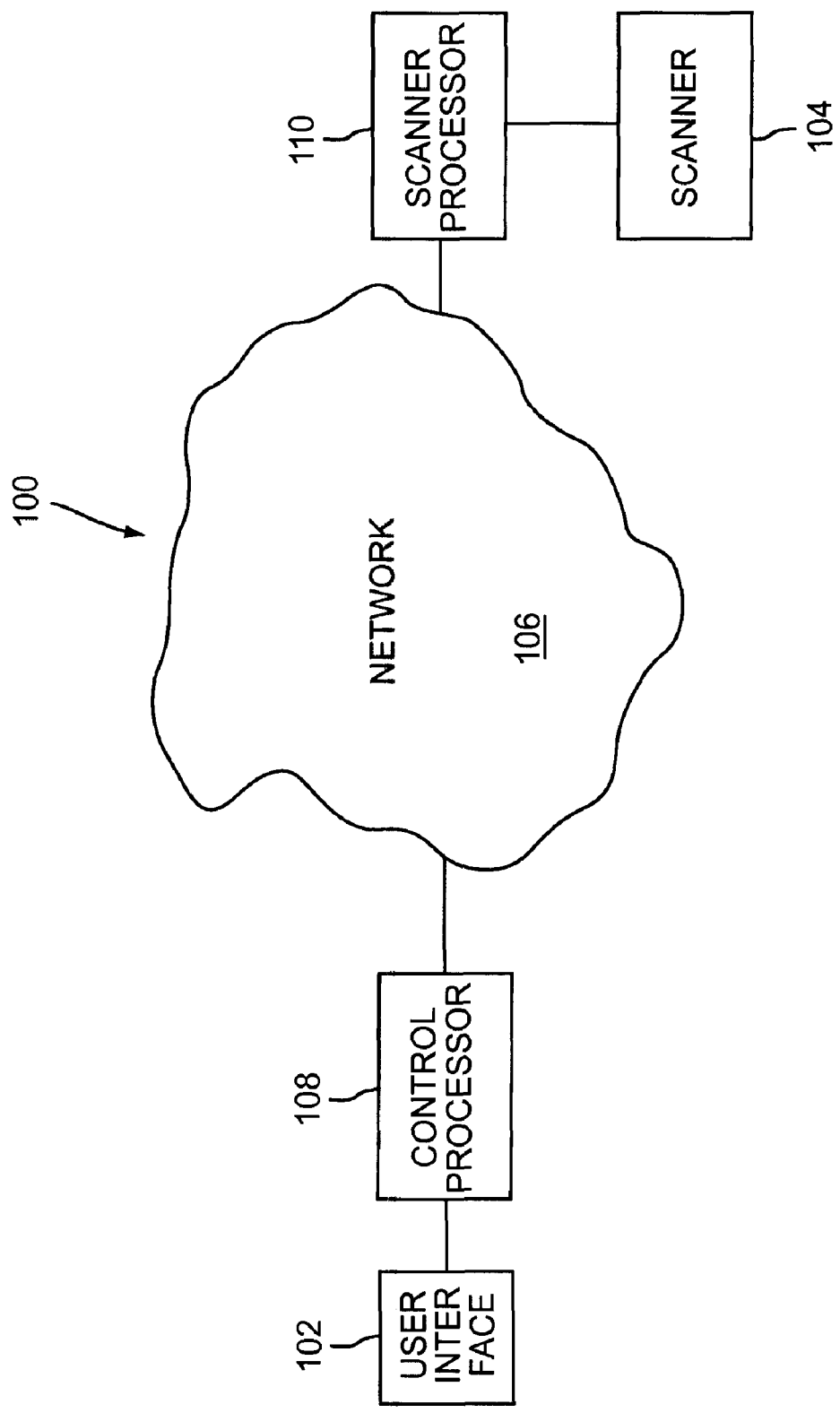
FIG. 1 is a block diagram showing an exemplary system according to the present invention, connecting a control space to a scan space.

Referring to FIG. 1, communication in the system of the present invention 100 generally takes place between a control user interface 102 and a scanner 104 via a network 106. It is contemplated that the network 106 can be a LAN, WAN, MAN, satellite network, an intranet, the Internet, or any other data network. The user interface 102 communicates with a control processor 108 to provide control data and other information onto the network 106. At the scanner side, the network 106 interfaces with a scanner processor 110, which communicates with the scanner 104. Thus, control data and image data are passed between the control user interface 102 and the scanner 104 via that network 106.

Figure 2:
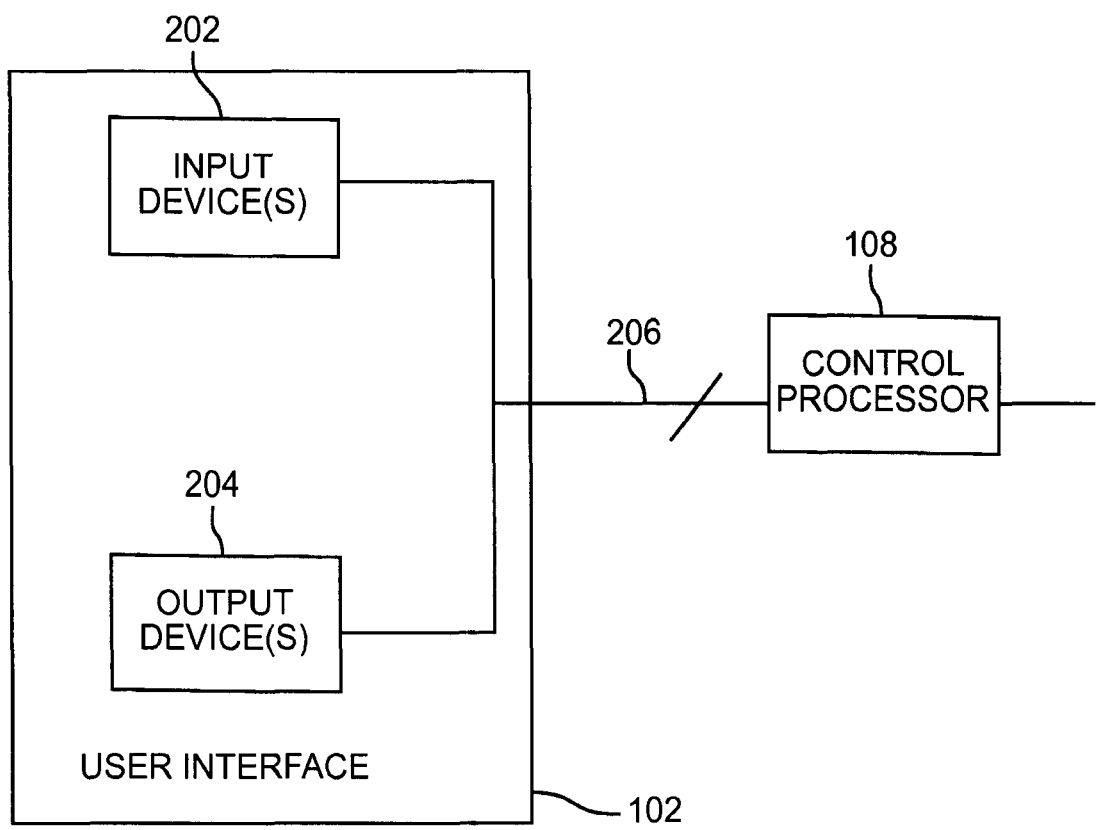
FIG. 2 is a block diagram showing detail of an exemplary user interface.

As shown in FIG. 2, the control user interface 102 can include one or more input devices 202 and one or more output devices 204. The input devices 202 can include a keyboard and cursor manipulation device, such as a mouse or trackball, for entering data such as control parameters and commands to be sent to the scanner. The input devices 202 can also include a microphone, so that the technician who is present at the user interface can provide information orally to the patient at the scanner, or to anyone who might be present locally at the scanner space. A still image or video capture device can also be provided as an input device 202 at the user interface 102, if an image is to be provided at the scanner space, such as identification information in graphical form for security reasons. Other input devices 202, such as a stylus and a touch screen grid, are contemplated for use at the user interface 102, depending on the data required to be entered for the particular application.

Images resulting from the scan, or from a scan that is locally controlled, can be remotely viewed via the network as well. Thus, an operator can remotely perform tasks that he or she would otherwise perform locally, that is, while physically present at the scanning center. The remote operator can set parameters, prepare patients, initiate scans, and monitor all activity at the site through use of video signals sent over the network. The present invention can be used by other medical personnel, such as radiologists to perform remote scans, physicians and surgeons to direct the scan procedure and make diagnoses, a scanning technician to operate more than one scanner, and research scientists to use remote scanners for research purposes.

Therefore, as shown in FIG. 2, the user interface 102 can include output devices 204, such as one or more video displays, in order to monitor activity at the scan center, or to view image data resulting from the scan. The output devices 204 can also include one or more audio speakers, so that the patient or personnel at the scan center can provide audible information to the remote scan operator. The audio speakers can also provide audio indications other than speech, such as a tone that indicates the completion of a scan procedure, or an alarm signal indicating a problem at the scan center.

The signals provided to the input devices 202 and the signals received by the output devices 204 are passed on a bus 206, or other transmission medium, to and from the control processor 108. The control processor 108 includes any circuitry or software necessary for properly processing signals from the input devices 202 for transmission on the network. The control processor 108 also includes any circuitry or software necessary for properly processing signals received over the network, such that these signals can be appropriately presented by the output devices 204. Thus, the control processor includes the modem or network interface card, a sound card or other sound processor, and a video card or other hardware or software necessary to present images to the user via the output devices 204. It is contemplated that the control processor 108 can be a component that is separate from the input and output devices 202, 204, and the control processor 108 itself can include more than one component, or can be distributed among more than one module. Likewise, any combination of input devices 202, output devices 204, and the control processor 108 or a control processor module can be integrated in a single component.

Figure 3:
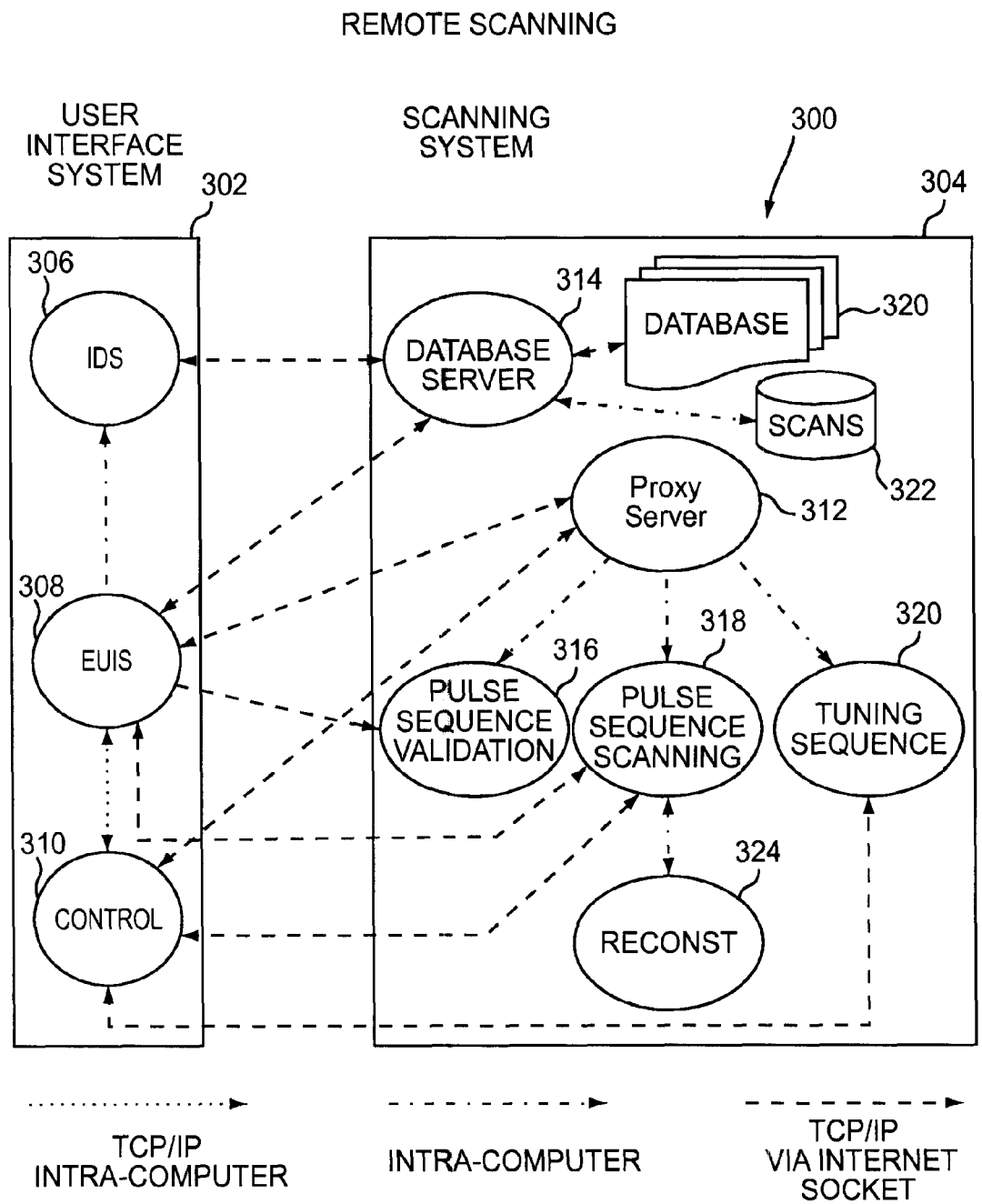
FIG. 3 is a block diagram showing communications aspects of an exemplary embodiment in which remote control of the scanner is effected.

More specifically, an exemplary embodiment in which remote control of the scanner is effected is shown in FIG. 3. As shown, the system 300 includes a user interface system 302 and a scanning system 304. The user interface system 302 includes an image display system (IDS) 306, an equipment user interface system (EUIS) 308, and a control system 310. Each of the systems included in the user interface system 302 can be realized at least in part in software. They can be implemented as separate software modules, can be combined in a single program, or can have functionality that is distributed among other programs. Likewise, they can be stored separately on individual storage media or they can be stored on the same storage medium, or any of them can be distributed among a number of different storage media.

The IDS 306 provides the remote technician with the ability to display, enhance, zoom, window, film, and otherwise manipulate images resulting from the scan. Thus, it preferably communicates with the scanning system 304 database server 314 over a network connection, such as via Internet socket using TCP/IP protocol. Within the user interface system 302, the IDS 306 receives commands from the EUIS 308. As shown, in the exemplary embodiment of FIG. 3, the database server 314 communicates with a database 320, which contains information about past scans and specifies where the corresponding images are stored. The database server 314 also communicates with the scan storage 322, which contains the image data resulting from the scan process. The IDS 306 in this embodiment has access to both the database 320 and the scan storage 322 through the database server 314. The database 320 and the scan storage 322 need not be embodied in singular respective devices, but rather can be distributed among more than one database and storage devices.

The EUIS 308 is the scanner control panel. It allows the remote operator to make entries in the scanner database, to enter scanning parameters, to initiate or terminate a scan, to display status information during a scan, and to transfer images to chosen destinations. Accordingly, the EUIS 308 provides control for the IDS 306, and also communicates with the scanning system 304 database server 314 via the network.

The control system 310 provides a finer level of control for the scanner, and is particularly advantageous for use by field engineers. The control system 310 allows the remote technician to adjust the RF power amplifier and the gain for the RF receiver, to view the NMR echo in both the frequency and time domains, and to adjust the scanning magnet's central frequency. The control system 310 also carries out communication with certain peripheral components of the scanning system 304. This communication takes place through the proxy server 312 resident at the scanning system 304, via the network. The proxy server 312 conducts serial communications sessions with local peripherals, so as to conduct, for example, pulse sequence validation 316, pulse sequence scanning 318, and a tuning sequence 320, on behalf of the control system 310. As shown in FIG. 3, the exemplary embodiment also includes a reconstruction module 324, which processes raw data generated during a scan sequence to provide final images to the pulse sequence scanning module 318.

According to a particular feature of the present invention, the local functions can determine whether they are running locally or under control of the remote system, and thus whether to communicate through the proxy server. In a particular embodiment of the present invention, this capability is provided by a library module that is included as part of the modules that are involved in communication between the user interface system 302 and the equipment system 304. The library module checks the network addresses of the modules or other components with which it is communicating. If the network address does not match that of known network addresses for local modules, the local function enters remote mode. Of course, certain safety features known to those skilled in the art can be implemented to ensure that the remote entity communicating with the local function is authorized to do so. For example, the library module can incorporate a firewall or blocking program that lists the network addresses for known remote modules. In the case of communication over the Internet, for example, lists of local and authorized remote IP addresses would be used to determine whether the local functions proceed in local mode or remote mode, or whether commands are blocked altogether. Logging capability and other advanced security features known to those of skill in the art can also be implemented.

As described, a number of systems, which can be implemented in software, reside on the user interface system and communicate with a number of systems, which also can be implemented in software, resident at the scanner processor. In the exemplary embodiment shown in FIG. 3, three systems, the IDS 306, the EUIS 308, and the control system 310, communicate with five systems, namely, the database server 314, the proxy server 312, the validation mode pulse sequence system 316, the scanning mode pulse sequence system 318, and the tuning sequence system 320, all of which can be implemented in software. The validation mode pulse sequence system 316, the scanning mode pulse sequence system 318, and the tuning sequence 320 are initiated by the EUIS through the proxy server 312, using a communications protocol that can be proprietary. Once initiated, the validation mode pulse sequence system 316, the scanning mode pulse sequence system 318, and the tuning sequence 320 can establish their own communications links with the user interface system 302, as shown in FIG. 3. In this way, the control system 310 functions as a hardware interface, and the proxy server 312 performs the input/output function for the local peripherals on behalf of the control system. In the exemplary embodiment shown in FIG. 3, for example, the proxy server 312 performs serial I/O with the validation mode pulse sequence system 316, the scanning mode pulse sequence system 318, and the tuning sequence 320 when prompted by the control system 310.

Figure 4:
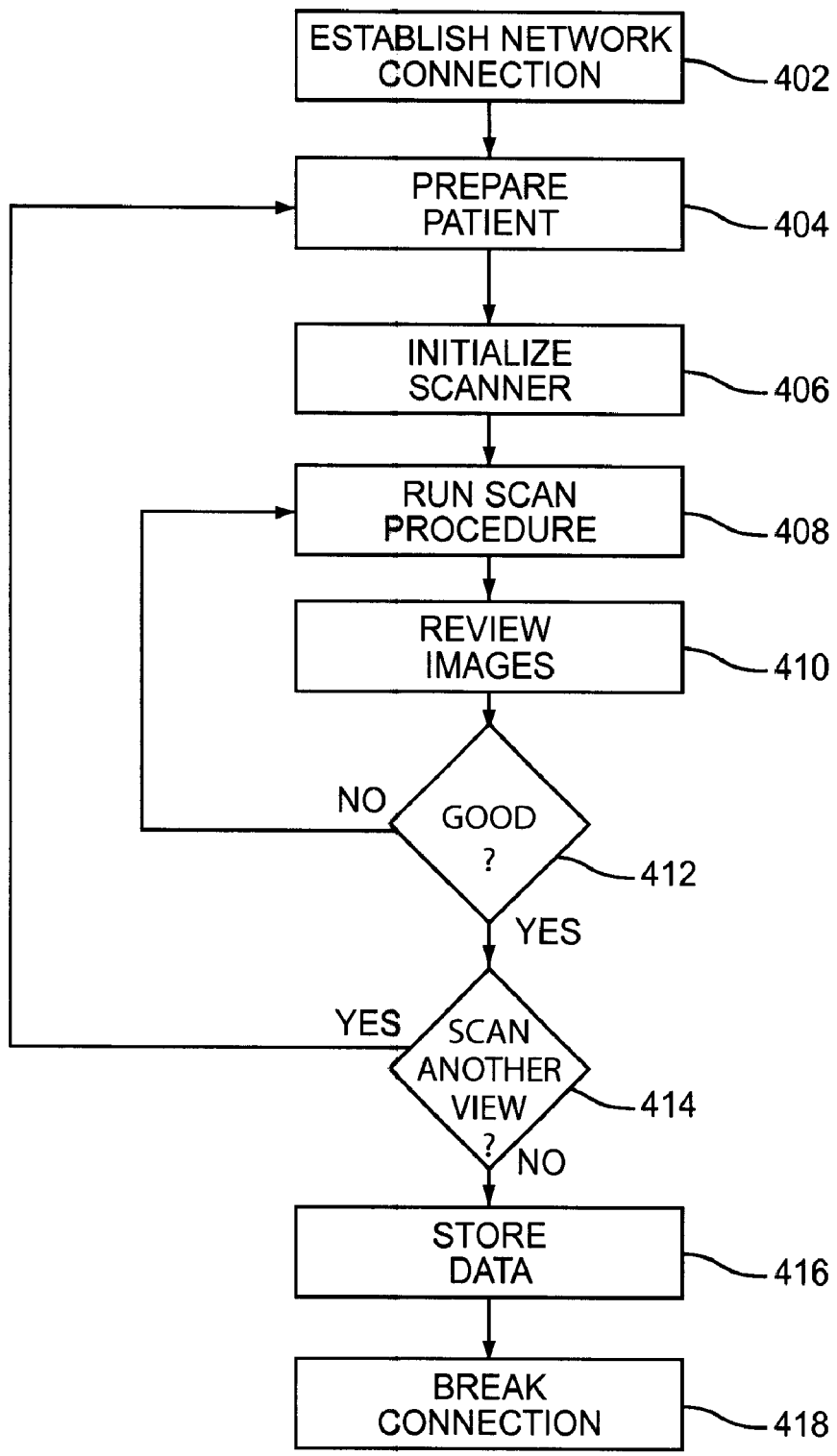
FIG. 4 is a flow diagram showing an exemplary process of the present invention.

Referring to FIG. 4, an exemplary process for remotely controlling the operation of an MRI scanner according to the present invention is shown in flow diagram form. As shown, before control of the scanner can be assumed remotely, a network connection must be established 402. That is, the control processor and the scanner processor must both be connected for communication over the network. As with a scan procedure that is controlled locally, the patient must be prepared for the scan 404. That is, the region of interest must be prepared, the patient must be positioned, and any other initial action involving the patient must be performed. Patient preparation can be performed prior to establishing the network connection, by personnel local to the scanner, such as a local assistant to the remote technician. However, there are advantages to preparing the patient after establishing the network connection. For example, the operator at the remote control space can, in some cases, prepare the patient by giving audio instructions to the patient over the network, and by monitoring the patient to insure that the instructions have been followed. Further, some scanners include features that are automated or mechanized and that are used to position the patient for a scanning procedure. For example, positioning a patient on a scanning bed is a local assistant task that is part of patient preparation. However, some scanning beds can be more accurately described as patient movement systems. Such systems are motorized platforms that can be positioned in a number of different ways, such as with respect to height, lateral angle, and rotational angle. Once the patient is placed on such a platform and secured by the local assistant, the mechanized adjustments can be performed remotely by the technician. After the positioning adjustments are made in such a system, the remote technician can control placement of the platform into the imaging volume.

The scanner is also initialized 406, either before or after preparing the patient, depending on the standard procedure at the scanner space. This can be performed locally, by a technician at the scanner space. Alternatively, this action can be taken by the remote operator, over the network, after establishing the network connection, in order to make greater use of the advantages of the present invention. Initialization of the scanner in this case takes place in a manner known to those skilled in the art to be conventional or standard, with the exception that the scanner is controlled remotely by signals sent by the remote scanner operator, rather than by a local operator.

Once the scanner is initialized, the patient is prepared, and the network connection is established, the scan procedure is run 408. As with initialization of the scanner, the scan procedure itself is that known to those of skill in the art, and differs from conventional or standard procedures in that the scanner is controlled remotely by signals sent by the remote scanner operator, rather than by a local operator. During the procedure, if the patient must be moved or the area of interest must be moved or turned for further scanning, the remote operator can provide audio instructions to the local assistant or the patient himself, and can monitor the patient's adherence to these instructions, all by way of audio and video signals transmitted over the network.

Further, as the scan procedure progresses, image data will be generated by the scanner. This image data can be transmitted over the network to the remote control space, where the data can be converted to images presented on a display to the remote operator. Thus, as the scan procedure takes place, the remote operator can review the images 410 corresponding to the image data generated by the scanner. As the images are reviewed, the operator might determine that one or more of the images are not good enough for use in making a reliable diagnosis. In making this determination 412, the operator must decide whether to continue with the process, or to run the scan procedure, or a portion of the scan procedure, again, in order to get better image data. If the scan is run again 408, the resulting images will once again be reviewed 410 and the quality determination will be made 412.

When the operator is satisfied with the quality of the images, a determination is made as to whether an additional scan, such as of another view, body part, or region of interest, will be made 414. If so, the patient is prepared for the next scan 404, and the procedure continues as described above. If another scan is not to be performed, or if the last scan procedure has been completed, data from the scan procedure is stored 416. This action can be taken at any point in the scan procedure, such as, for example, after the scan procedure has been completed for a first view and prior to performing a second scan procedure. Further, the scan data can be stored locally at the scan center, at the remote control space, at a third location designated for scan data storage, or in duplicate at any combination of these locations. The scan data can be stored at the designated location(s) by default, or under the control of the remote scan operator. Alternatively, a default can be set up for scan data storage location, and this default can be overridden by action of the remote scan operator.

After the scan procedure has been completed, the network connection can be broken 418. Prior to breaking the network connection, the patient can be remotely guided through any follow-up procedures. Likewise, the scan equipment can be shut down, following standard procedure under the control of signals transmitted by the operator at the remote control space. Alternatively, these final actions can be undertaken by local personnel, and the network connection can be broken at any time following the scan procedure.

While transmission of audio signals and video signals related to the monitoring of the scan space are generally straight-forward, transmission of signals to the scan space from the control space requires a message format, or protocol, that is recognized by both the control processor and the scan processor. This format includes data fields to provide information needed at the scan space to perform the scan procedure. For example, parameters such as scan sequence selection, field of view, slice thickness, number of slices, and number of excitations are required by the scanner in order to perform a particular scan procedure. Further, "start", "pause", and "stop" protocols must be established and, depending on the level of sophistication of the scanner used, "repeat" and similar instructions might be provided. One known manner of setting up such a message format is to define a message body having several fields, each denoting particular actions or parameters designated at the control space and interpreted at the scan space. The particular protocol used in conjunction with the present invention is not important, as long as it is consistent, and provides the information necessary to perform the scanning procedure.

Figure 5:
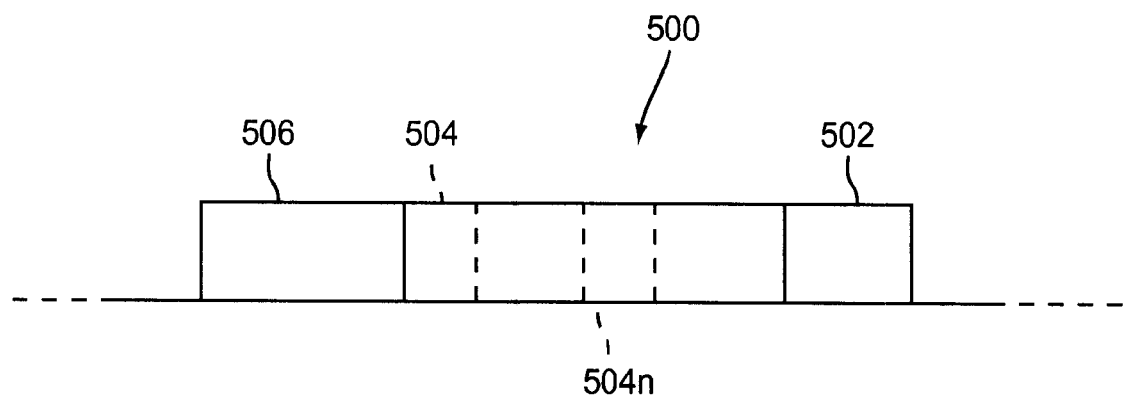
FIG. 5 is a timing diagram of an exemplary data structure of the present invention.

For example, an exemplary data format is shown in FIG. 5. As shown, the exemplary format for the message 500, or data structure, includes a header 502 and substantive data 504. A check field 506 can also be provided. The header 502 includes information identifying the type of substantive data to follow. For example, during initialization of the scanner 406, certain parameters related to the type of scan procedure to be performed, such as scan sequence selection, field of view, slice thickness, number of slices, and number of excitations, must be provided to the scan processor 110. Thus, the header would identify that the substantive data to follow consists of initialization parameters. The control processor would construct the header to provide this information, and the scan processor would be programmed to recognize it. The substantive data field 504 would then provide this data. The substantive data field 504 can be divided into sub-fields 504n, each of which provides a particular type of parameter. Again, programming of the control processor and the scan processor provide consistency such that the scan processor knows in which sub-field to find the particular parameter inserted by the control processor, at the instruction of the control operator.

Once the scanner has been initialized, certain instructions can be provided to the scanner during the procedure itself. Again, this can be effected by providing a header that identifies the substantive data to follow as scan instructions, where the substantive data field is divided into sub-fields that identify each particular instruction. If a shut-down procedure for the scanner is controlled by the remote operator, a header and substantive data field related to this procedure are designated as well.

In order to provide a level of assurance that control signals are transmitted and received properly, a check field 506 can be provided. Such check fields, such as parity checks and cyclical redundancy checks, are known in the telecommunications arts, and indicate whether transmission errors caused by, for example, noise on the network, resulted in corruption of the transmitted data.

More specifically, according to an exemplary embodiment of the present invention, the system 300 builds its own protocol communications packets. In the exemplary embodiment shown in FIG. 3, for example, in which communication between the user interface system 302 and the scanning system 304 can take place via the Internet, the protocol communications packets are placed within standard TCP/IP formatting. These packets constitute a protocol that is specific to the vendor of the MRI scanning equipment, and include both command information and corresponding data. For example, for a command to run a scan, the protocol would include a run command, the complete path to the scan program to be run, and any command line arguments. Likewise, a command to terminate a scan would include similar information and data, specific to the terminate command.

According to the process described above, a radiologist or scanning technician in one location can control and supervise the operation of a scanner in another location, regardless of the distance. In addition, a scanning technician can operate many scanning centers from a central location, thereby reducing the overall operating expenses of the scanning centers. The remote control space can make and break network connection with any of the scan locations in order to control scanners at those locations, and, with the proper bandwidth and equipment, can control scan procedures at more than one location at a time.

Figure 6:
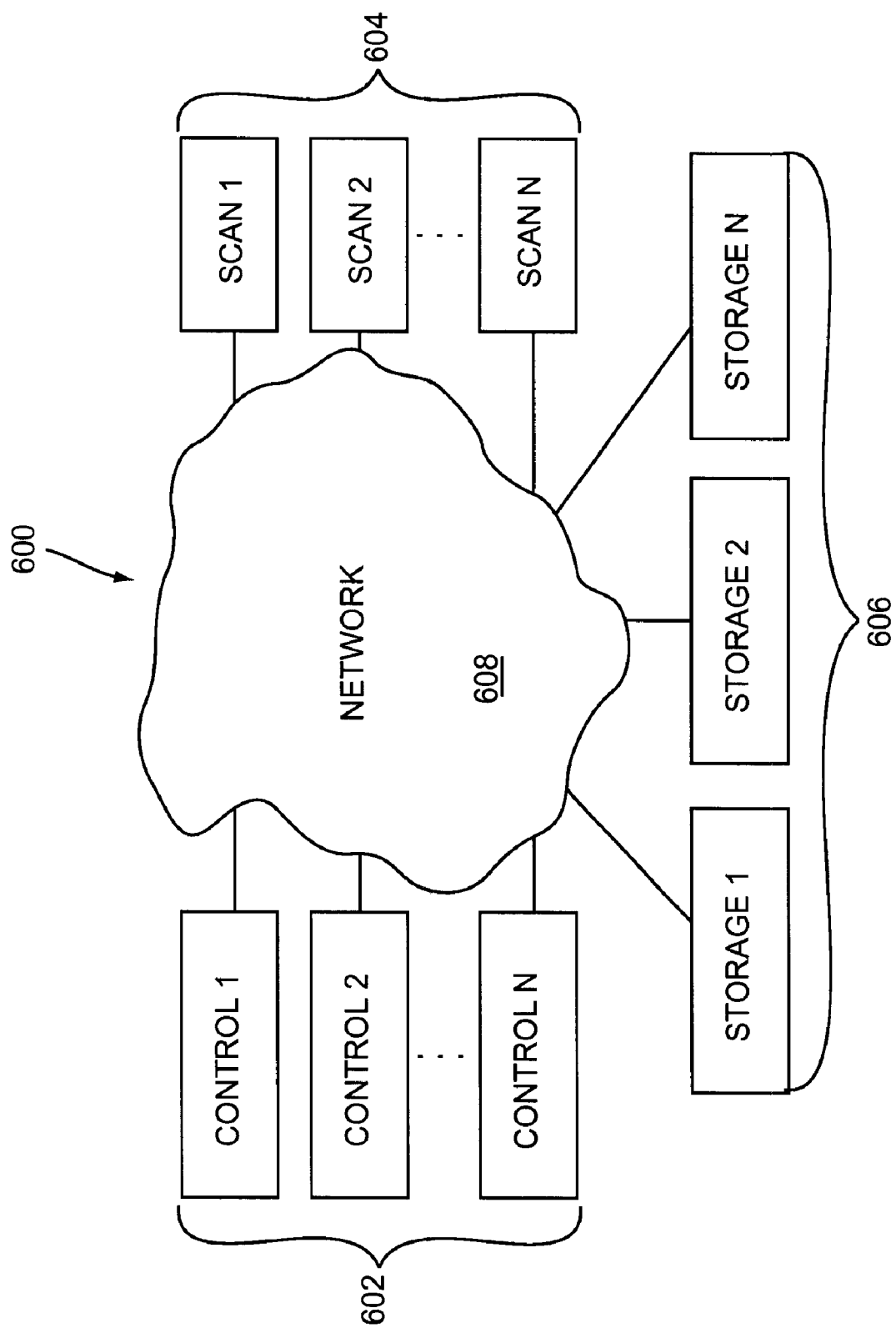
FIG. 6 is a block diagram showing a general set-up of an exemplary cooperative business method of the present invention.

In the most general sense, as shown in FIG. 6, the system of the present invention 600 can include any number of control spaces 602, any number of scan spaces 604, and any number of storage spaces 606, all connected by a network 608. Connected in this manner, a cooperative business method is devised by which resources can be pooled among a number of scan centers, control centers, and storage centers, each of which can be located remotely from any of the others in a geographic sense. Thus, with trained technicians present at the control centers, any combination of the connected resources can be used to remotely perform scanning procedures and direct storage of the resulting image data.

Figure 7:
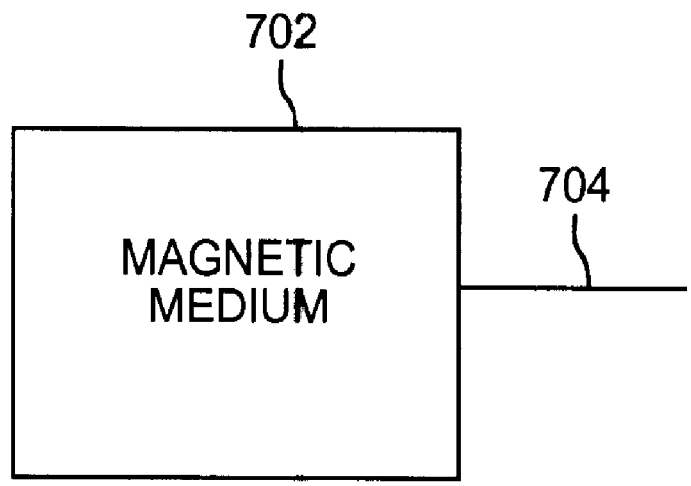
FIG. 7 is a block diagram of an exemplary magnetic medium of the present invention.

A stated previously, the systems present at the user interface system 302 and the scanning system 304, such as the EUIS 308 and the proxy server 312, can be implemented in software, in the form of instructions for causing a data processor to perform certain functions. These instructions must be stored on some medium at the appropriate location. As shown in FIG. 7, these instructions can be stored on any type of medium 700, such as magnetic or optical media, which can interface via a port 704 with the data processor included in the control and scan processors, and at any remote storage spaces that might be provided. The storage medium can be memory provided internal to the processor, or can be any of the variety of storage media known to those skilled in the art that can be provided external to the processor, including any of various available portable storage media.

Particular exemplary embodiments of the present invention have been described in detail. These exemplary embodiments are illustrative of the inventive concept recited in the appended claims, and are not limiting of the scope or spirit of the present invention as contemplated by the inventors. For example, the system and processes described are advantageous for use with any medical diagnostic procedure that conventionally requires a skilled local technician to process a patient and administer the procedure. Thus, although the example of an MRI scanning environment has been described to facilitate disclosure of the present invention, it is not contemplated that the invention is limited to only this application. Further, the exemplary embodiment utilizes the Internet for communication between the user interface system and the scanning system. However, it is contemplated that the local system and the remote system can communicate over any network, or via a dedicated communications channel that can be wired, such as by electrical or optical cable, or wireless, such as by satellite. In addition, the functionality of certain elements of the present invention, such as the proxy server, can be present in or enabled by the operating system resident on the respective processor, and need not be a program that exists or runs independently of the operating system or other application or utility present at the processor. Still further, applications for the present invention are not limited to diagnostic procedures. The system of the present invention can be used, for example, by field service personnel for maintenance or repair of MRI scanners or other medical equipment, or by research organizations such as universities.

What is claimed is:

1. A system for controlling functionality of local interactive equipment from a location that is remote from the equipment, comprising:
   a remote user interface that accepts inputs from a remote user and provides corresponding user input signals;
   a control processor, in communication with the remote user interface, that receives the user input signals and formats the user input signals for transmission;
   an equipment processor, in communication with the local interactive equipment, that receives the formatted user input signals and controls the local interactive equipment based on at least some of the formatted user input signals; and
   a communications channel that provides a communications capability between the control processor and the equipment processor, such that the formatted user input signals can be transmitted from the control processor to the equipment processor;
   wherein the local interactive equipment is one of medical diagnostic equipment and medical screening equipment; and
   wherein the equipment processor includes a proxy server that receives the formatted user input signals and controls the local interactive equipment based on at least some of the formatted user input signals.

2. The system of claim 1, wherein the proxy server translates said at least some of the formatted user input signals to provide control inputs for the local interactive equipment.

3. The system of claim 2, wherein the equipment processor includes at least one peripheral module.

4. The system of claim 3, wherein said at least one peripheral module includes at least one of a validation pulse sequence module, a scanning pulse sequence module, and a tuning sequence module.

5. The system of claim 3, wherein the user interface communicates with the at least one peripheral module via the proxy server.

6. The system of claim 5, wherein the proxy server conducts serial communication with said at least one peripheral module for the remote user interface.

7. The system of claim 2, wherein the user remote interface includes an equipment user interface that provides formatted operational user input signals to the proxy server, wherein said at least some of the formatted user input signals include the formatted operational user input signals.

8. The system of claim 7, wherein the formatted operational user input signals control at least initiation and termination of procedures performed by the local interactive equipment.

9. The system of claim 7, wherein the formatted operational user input signals include operational parameters used by the local interactive equipment.

10. The system of claim 2, wherein the remote user interface includes a control module that provides formatted adjustment user input signals to the proxy server, wherein said at least some of the formatted user input signals include the formatted adjustment user input signals.

11. The system of claim 10, wherein the formatted adjustment user input signals include at least one of a power amplifier adjustment, a receiver gain, and a central frequency.

12. The system of claim 11, wherein the equipment processor includes at least one peripheral module.

13. The system of claim 12, wherein said at least one peripheral module includes at least one of a validation pulse sequence module, a scanning pulse sequence module, and a tuning sequence module.

14. The system of claim 12, wherein the control module communicates with the at least one peripheral module via the proxy server.

15. The system of claim 14, wherein the proxy server conducts serial communication with said at least one peripheral module for the control module.

16. The system of claim 10, wherein the control module is adapted to provide the formatted adjustment user input signals having a communications protocol for transmitting and receiving the control signal from the remote location to the local interactive equipment over a communications channel, and operational information used by the local interactive equipment for controlling the local interactive equipment.

17. The system of claim 16, wherein the operational information is grouped in packets that are wrapped in the communications protocol.

18. The system of claim 16, wherein the communications channel is a data network, and the communications protocol includes information necessary for data transmission over the data network.

19. The system of claim 18, wherein the data network is the Internet, and the communications protocol is TCP/IP.

20. The system of claim 16, wherein the communications channel is a satellite link, and the communications protocol includes information necessary for data transmission over the satellite link.

21. The system of claim 16, wherein the operational information includes at least one of command information and parameter data.

22. The system of claim 21, wherein the command information includes at least one of
   a run command, to initiate a diagnostic procedure at the local interactive equipment; and
   a terminate command, to terminate a diagnostic procedure at the local interactive equipment.

23. The system of claim 21, wherein the parameter data includes at least one of scan sequence selection, field of view, slice thickness, number of slices, and number of excitations.

24. The system of claim 16, wherein the operational information is specific to a manufacturer of the local interactive equipment.

25. The system of claim 16, wherein said one of medical diagnostic equipment and medical screening equipment is an MRI scanner.

26. The system of claim 16, wherein the control signal is a remote user input signal that controls the functionality of the local interactive equipment.

27. The system of claim 26, wherein the user input signal controls all the functionality of the local interactive equipment.

28. The system of claim 26, wherein the user input signal controls the functionality of the local interactive equipment without the need for local user input to the local interactive equipment.

29. The system of claim 26, wherein the user input signal controls the functionality of the local interactive equipment without the need for local user input to the system.

30. The system of claim 16, wherein the control signal includes a component that distinguishes for remote control a selected unit of interactive equipment from among a plurality of units of interactive equipment.

31. The system of claim 30, wherein each said unit of interactive equipment is located in a different respective location.

32. The system of claim 16, wherein communication over the communications channel is controlled by a user at the remote location.

33. The system of claim 32, wherein all communication over the communications channel is controlled by the remote user.

34. The system of claim 16, wherein the control signal is generated at the remote location.

* * * * *